United States Patent [19]
Hardy et al.

[11] Patent Number: 6,083,694
[45] Date of Patent: *Jul. 4, 2000

[54] METHOD FOR ELUCIDATION AND DETECTION OF POLYMORPHISMS, SPLICE VARIANTS, AND PROXIMAL CODING MUTATIONS USING INTRONIC SEQUENCES OF THE ALZHEIMER'S S182 GENE

[75] Inventors: John Hardy, St. Augustine, Fla.; Alison M. Goate, Richmond Heights, Mo.

[73] Assignees: University of South Florida, Tampa, Fla.; Washington University, St. Louis, Mo.

[*] Notice: This patent issued on a continued prosecution application filed under 37 CFR 1.53(d), and is subject to the twenty year patent term provisions of 35 U.S.C. 154(a)(2).

[21] Appl. No.: 08/738,381

[22] Filed: Oct. 25, 1996

Related U.S. Application Data

[60] Provisional application No. 60/007,048, Oct. 25, 1995, abandoned.
[51] Int. Cl.[7] .............................. C12Q 1/68; C12P 19/34; C07H 21/04
[52] U.S. Cl. .................... 435/6; 435/91.2; 536/24.31; 536/24.33
[58] Field of Search ................... 435/6, 91.2; 536/24.33, 536/24.31; 935/8, 78

[56] References Cited

U.S. PATENT DOCUMENTS

| | | | |
|---|---|---|---|
| 5,840,540 | 11/1998 | St. George-Hyslop et al. | 435/69.1 |
| 5,853,988 | 12/1998 | Dryja et al. | 536/23.1 |

OTHER PUBLICATIONS

Cribbs et al. "Widespread Neuronal Expression of the *presenilin–1* Early–Onset alzheimer's Disease Gene in the Murine Brain", American Journal of Pathology, vol. 148 (6), pp. 1797–1806 (1996).
Rogaev et al. "Familial Alzheimer's disease in kindreds with missense mutations in a gene on Chromosome 1 related to the Alzheimer's disease type 3 gene", Nature, vol. 376, pp. 775–778 (1995).
Slunt et al. Amyloid. 2(3): 188–190, Sep. 1995.
Sherrington et al. Nature. 375: 754–760, Jun. 1995.
Cai et al. American Journal of Medical Genetics. 74: 202–203, 1997.
Scott et al. Genetic Epidemiology. 14:307–315, 1997.
Clark et al. Nature Genetics. 11:219–222, Oct. 1995.

*Primary Examiner*—Carla J. Myers
*Attorney, Agent, or Firm*—William T. Han; Ratner & Prestia; Wlllliam T. King

[57] ABSTRACT

A method of detecting polymorphisms in the S182 gene by detecting mutations in the S182 gene using selected mismatched PCR primers comprising sequences derived from intronic sequences of the S182 gene is provided. A method of identifying an individual susceptible to late onset Alzheimer's Disease is also provided.

7 Claims, 3 Drawing Sheets

Exon 2 (to -53)
ATAAAGAAAGgtttgtttctgcttaatgta

Exon 3 (-52 to 12)
AGCAATACTGTACGTAGCCAGgtacagtgt

Exon 4 (76 to 326)
GGGCAGCTgtacgtatgagatttgtttt

Exon 5 (327 to 468)
TGCTATAAGgtgagcatgagacacagatc

Exon 6 (469 to 536)
TACTTGGGgtaagttgtgaaattttgg

Exon 7 (537 to 751)
TCAGTATATGgtaaaacccaagactgataa

Exon 8 (757 to 856)
ATTTACTCCTgtaagtatttgagaaggata

Exon 9 (857 to 942)
AATGCAGAAgtaggtaactttattagat

Exon 10 (943 to 1117)
CCAGAGGAAAgtatgtgcatttctctatgt

Exon 11 (1118 t 1236)
ATATTAATTgtaagtatacactaataaga

Exon 3
gttttttctttcccttttcagAACCTCAAGA

Exon 4
tgtttttcttgtgcttatagAATGACAAT

Exon 5
ttgtgtttgttttattgtagAATCTATAC

Exon 6
tgaaatgctttcttttctagGTCATCCAT

Exon 7
tctgtgtaattttttttcagGGAACTGTT

Exon 8
ttatgtttttcttttctagATTTAGTGG

Exon 9
aatttngtctttcccaacagCAACAATG

Exon 10
acttccactttctcttgaaGCACAGAAG

Exon 11
ttgtaacctttccttttagGGGGAGTA

Exon 12 (1237 - 3' end)
ctttcccatcttctccacagGGTTTGTGC

```
            Exon8              Exon9                Exon10
         IleTyrSerS|erThrMet.....AsnAlaGluS|erThrGlu
wild type ATTTACTCCT|CAACAATG.....AATGCAGAAA|GCACAGAA F74       ATTTACTCCT|GCACAGAA.....CCAGAGGAAA|GGGGAGTA
         IleTyrSerC|ysThrGlu.....ProGluGluA|rgGlyVal
            Exon8              Exon10               Exon11
```

FIG. 2C

METHOD FOR ELUCIDATION AND DETECTION OF POLYMORPHISMS, SPLICE VARIANTS, AND PROXIMAL CODING MUTATIONS USING INTRONIC SEQUENCES OF THE ALZHEIMER'S S182 GENE

This application claims the benefit of U.S. Provisional Application No. 60/007,048, now abandoned, filed on Oct. 25, 1995.

BACKGROUND OF THE INVENTION

Alzheimer's disease (AD) is a progressive degenerative disease of the central nervous system characterized clinically by dementia and neuropathologically by the presence of numerous senile plaques and neurofibrillary tangles. AD is typically a late onset disease of the elderly. However, a small number of pedigrees have been described wherein an early onset form of the disease is inherited as an autosomal dominant with age dependent penetrance. Most commonly, the age of onset of the disease is below 60 years old. Genetic factors have been implicated in both early and late onset AD.

Mutations in at least four different genetic loci are associated with an inherited susceptibility to AD. The e4 allele of the apolipoprotein E (ApoE) gene on chromosome 19 is associated with late onset AD (Strittmatter et al. *Proc. Natl. Acad. Sci. USA* 1993, 90:1977–1981; Saunders et al. *Neurology* 1993, 43:1467–1472); Corder et al. *Science* 1993, 261:921–923). Mutations in the β-amyloid precursor protein (βAPP) gene on chromosome 21 have been found in a small number of families with early onset AD (Goate et al. *Nature* 1991, 349:704–706; Chartier-Harlin et al. *Nature* 1991, 353:844–846; Murrell et al. *Science* 1991, 254:97–99; Karlinsky et al. *Neurology* 1992, 42:1445–1453). Most recently, a novel AD locus in a gene referred to as STM2 was identified on chromosome 1 (1q31-41) from genetic linkage analysis of "Volga German" kindred (Ephrat Levy-Lahad et al. *Science* 1995, 269:970–973; ibid. 973–977). The STM2 gene bears a remarkable similarity to the AD-associated gene, S182.

The fourth locus (AD3) has been mapped by genetic linkage studies to chromosome 14q24.3 and may account for Lip to 70% of early-onset autosomal dominant AD. Schellenberg et al. *Science* 1992, 258:668–670; George-Hyslop et al. *Nature Genet.* 1992, 2:330–334; Van Boreckhoven et al. *Nature Genet.* 1992, 2:335–339). The AD3 locus is associated with the most aggressive form of this disease (onset between 30 and 60 years of age) and it has been suggested that mutations at this locus put into effect a biologically fundamental process leading to AD.

Recently, a novel gene with five missense mutations in seven pedigrees segregating early-onset autosomal dominant AD at the AD3 locus, the S 182 gene, was cloned and described by Sherrington et al. *Nature* 1995, 375:754–760. Analysis of the nucleotide sequence of the S182 transcript revealed heterozygous nucleotide substitutions in the reverse transcriptase-polymerase chain reaction products from affected members of six large pedigrees. The putative open reading frame (ORF) of S182 encodes a protein predicted to be a classical seven-transmembrane protein and the pedigree-associated nucleotide substitutions change the encoded amino acids in transmembrane (TM) helices II(L146M), VI(E246A), and VII(Y410C) and in loops between TMII-TMIII(R163H) and TMVI-TMVII(V286L). No transmembrane ion channel function has been demonstrated for S182 to date.

A number of other mutants of the S182 gene have now been identified. Genomic analysis of the S182 gene has defined the intron-exon boundaries of the primary transcription unit. This has led to the development of a method for identification of intronic polymorphisms which are predictive of disease as well as elucidation of several splicing variants and proximal coding mutations. These intronic sequences are useful in the early detection of mutant forms of the S182 gene, a gene which is usually associated with aggressive early-onset AD but may also be involved in the late onset of this disease as well.

SUMMARY OF THE INVENTION

An object of the present invention is to provide the sequences of the intron-exon boundaries of the S182 gene.

Another object of the present invention is to provide a method for the elucidation, detection, and diagnosis of mutations in both intronic sequences associated with splice variation and in the open reading frames proximal to these intron-exon boundaries of the S182 gene through use of intronic sequences.

Yet another object of the present invention is to provide the sequence of novel S182 mutations and to provide a method for their detection and diagnosis.

BRIEF DESCRIPTION OF THE FIGURES

FIGS. 2A, 2B and 2C provide diagrams of the location of the F74 (and possible F184) intronic mutations.

DETAILED DESCRIPTION OF THE INVENTION

Genetic linkage strategies placed a gene causing early onset familial Alzheimer's disease (FAD) on the long arm of chromosome 14 between D14S289 and D14S61. Five mutations within the S182 gene, which map to this region were recently reported in several families multiply affected by early onset AD (between 30–50 years) (Sherrington et al. *Nature* 1995, 375:754–760). While conventionally this gene has been thought to only be involved in the rare, familial early onset form of the disease, some evidence for allele sharing between affected family members with late onset disease has also been observed (Schellenberg et al. *Am. J. Hum. Genet.* 1993, 53:619–628). This allele sharing between affected family members was not found when standard maximum likelihood methods were used, but was found when the affected pedigree member method of genetic analysis was used, suggesting that the locus was not behaving as an autosomal dominant in the late onset form of the disease.

During sequence analysis of early onset Alzheimer disease cases, a common polymorphism within the intron 3' to exon 9 of the S182 gene was identified. The most common allele has an A at nucleotide 16 (allele 1) in the intron while the variant allele has a C at this position (allele 2). The present invention provides a method of detecting this polymorphism utilizing mismatch PCR primers which introduce a BamHI site when the variant C is at nucleotide 16, but not when the A is present. This allows for the rapid analysis of a large number of samples using PCR followed by digestion with the restriction enzyme for BamHI and agarose gel electrophoresis.

Digestion refers to catalytic cleavage of a nucleic acid sequence with a restriction enzyme that acts only at certain sites in the sequence. Restriction enzymes such as that for BamHI are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., *Nucleic Acids Res.* 1980, 8:4057.

The method of the present invention was used to screen for the presence of this polymorphism in a clinical series of AD cases and age matched controls. This polymorphism shows a strong association with the occurrence of typical late onset Alzheimer's disease, with homozygosity for the more common of the two alleles causing an apparent doubling of the risk for this form of the disease (Table 1). Table 1 illustrates the association of the presence of an intronic polymorphism in homozygous form with the occurrence of typical late onset AD.

TABLE 1

| Alleles | 11 | 12/22 |
| --- | --- | --- |
| control | 51(0.27) | 134(0.73) |
| AD | 89(0.43) | 119(0.57)[a] |
| familial | 14(0.44) | 18(0.56)[b] |

[a]cases v. controls chi squares=9.89, 1df, p=0.0012, OR=1.97, CI=1.29-3.00
[b]familial cases v. controls chi squares=3.40, 1df, p=0.065, OR=2.04, CI=0.95-4.41

This polymorphism does not change the coding sequences of the gene and in the clinical cases examined does not appear to alter the protein. It does, however, indicate that the S182 gene is involved in the pathogenesis of at least a proportion of late onset AD cases. Furthermore, if the polymorphism itself is of biological relevance, it may act by alternative splicing in this area.

Figure 1:
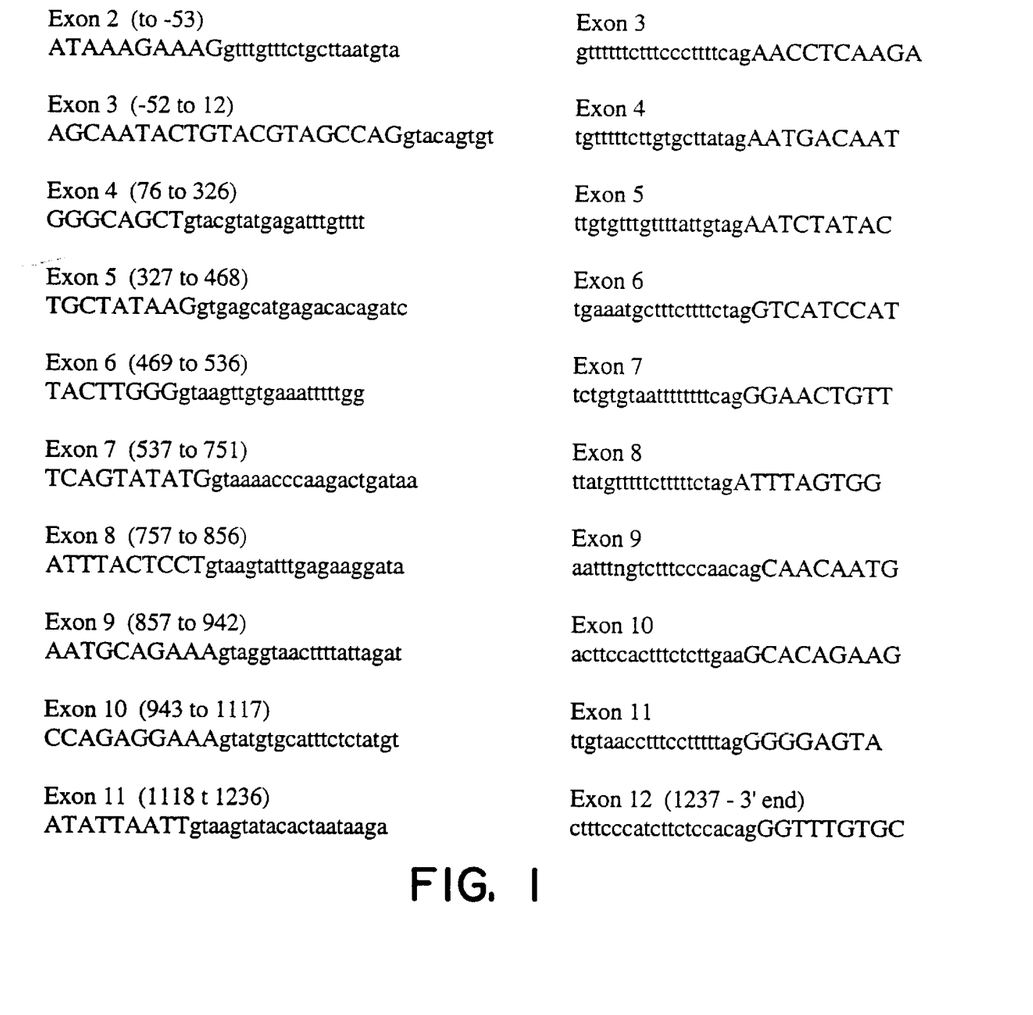
FIG. 1 illustrates the sequence of the intron exon boundaries of the S182 gene. Coding sequences are in uppercase letters, intronic sequences in lowercase letters. (Seq. I.D. Nos. 23–42)

Intronic sequences in other areas of the S182 are believed to be important for similar reasons. A full-length clone of S182 was isolated from human cerebellar cDNA libraries. The entire intron-exon structure of this S182 gene was determined by comparison of cDNA and genomic DNAs (FIG. 1). The S182 intronic sequences and their reverse complements near the intron-exon boundaries for the 12 exons were determined and are shown in Table 2.

TABLE 2

| Region | Sequence (5'->3') | |
| --- | --- | --- |
| Exon | gtttgtttctgcttaatgta | (Sequence ID NO: 1) |
| 2-3 | gtttttctttccctttcag | (Sequence ID NO: 2) |
| Exon | gtacagtgt | (Sequence ID NO: 3) |
| 3-4 | tgtttttcttgtgcttatag | (Sequence ID NO: 4) |

TABLE 2-continued

| Region | Sequence (5'->3') | |
| --- | --- | --- |
| Exon | acgtatgagatttgtttt | (Sequence ID NO: 5) |
| 4-5 | ttgtgtttgtttttattgtag | (Sequence ID NO: 6) |
| Exon | gtgagcatgagacacagatc | (Sequence ID NO: 7) |
| 5-6 | tgaaatgctttctttctag | (Sequence ID NO: 8) |
| Exon | gtaaaacccaagactgataa | (Sequence ID NO: 9) |
| 7-8 | ttatgttttttcttttctag | (Sequence ID NO: 10) |
| Exon | gtatgtgcatttctctatgt | (Sequence ID NO: 11) |
| 9-10 | ttgtaacctttcctttttag | (Sequence ID NO: 12) |
| Exon | gtatgtgcatttctctatgt | (Sequence ID NO: 13) |
| 10-11 | ttgtaacctttcctttttag | (Sequence ID NO: 14) |
| Exon | gtaagtatacactaataaga | (Sequence ID NO: 15) |
| 11-12 | ctttcccatcttctccacag | (Sequence ID NO: 16) |

Figure 2A:
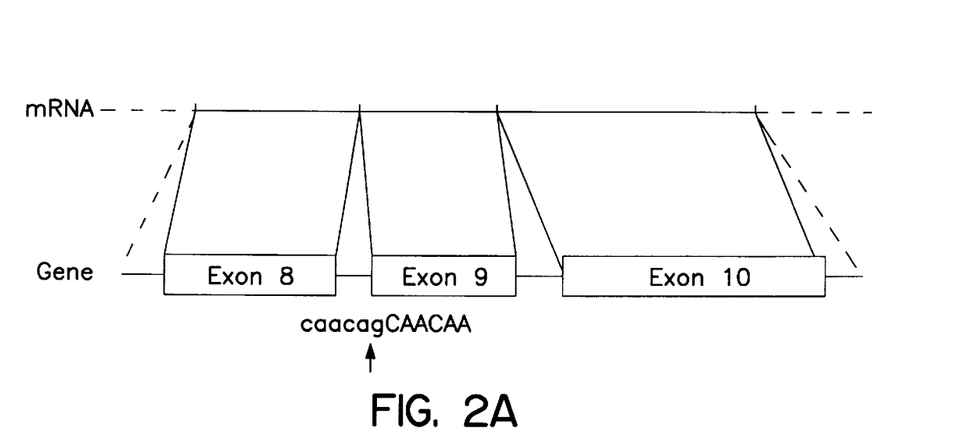
FIG. 2A shows the normal splicing of exon 9.
Figure 2B:
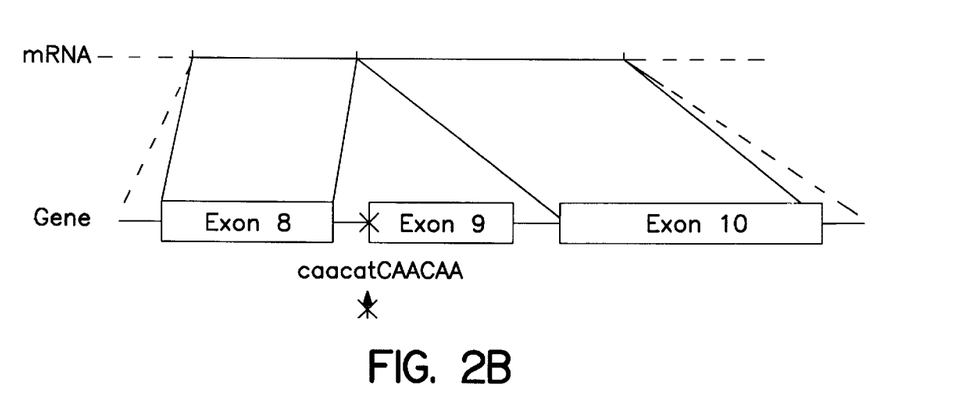
FIG. 2B shows the splicing of mutant PS-1 allele in F74 resulting in the loss of exon 9.
Figure 2C:
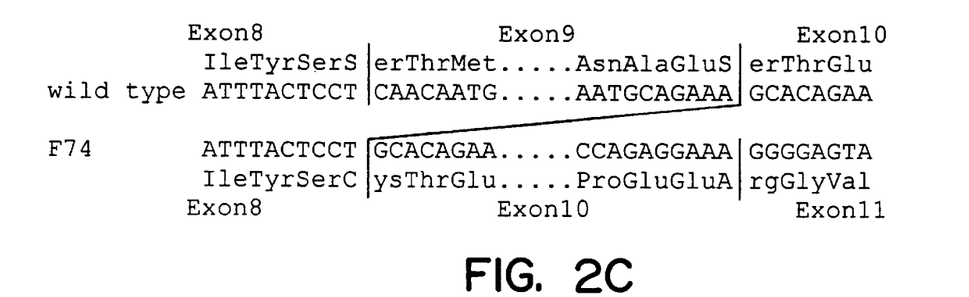
FIG. 2C provides a comparison of wild type and F74 mRNA and amino acid sequences. (Seq. I.D. Nos. 43–52)

Analysis of the intron-exon boundaries of the novel S182 gene indicated that a novel alternative splicing variant of the S182 gene had been expressed. Furthermore, using these primers, a mutation in the last nucleotide of the intron between exons 8 and 9 was found in at least one early onset AD family (F74) (FIG. 2). A novel mutation was identified in exon 5 which would have been impossible to detect without intronic sequences.

Identification and analysis of mutants or variants arising from mutations in splice donor or acceptor sites are enabled by knowledge of these intronic sequences. Furthermore, a complete analysis of the intron-exon boundaries makes possible sequencing primers that would allow accurate sequence determination of the first or last 10 to 20 nucleotides of coding exons especially near cDNA termini.

The following examples are provided for illustrative purposes only and are not intended to limit the invention.

EXAMPLES

Example 1

Screening Protocol for the T→G Polymorphism 3' of Exon 9

A mismatch primer was designed which contained two mismatched base pairs four and five base pairs away from the 3' end of the primer and five and six base pairs from the polymorphism. When incorporated in a PCR product, this primer produces a BamHI cut when G is present and no cut when T is present at the polymorphism site. This enables the two alleles to be distinguished by digestion of a PCR product with BamHI. Forward primer is 5'CACCCATTTA-CAAGTTTAGC3' (SEQ ID NO: 17) and the reverse primer is 5'CACTGATTACTAATTCAGGATC3' (SEQ ID NO: 18). This produces a PCR product of 200 bp which is cleaved by BamHI to produce fragments of 182 and 18 bp. DNA (50–100 ng) was used as a template in 25 μl reactions. The reaction mix consisted of the following concentrations: 0.2 mM dNTP's, 30 pM primer, 1X TNK50 buffer, 0.5 U Taq DNA polymerase. PCR was carried out under the following conditions: 94° C. for 5 minutes; 94° C. for 30 seconds; 45° C. for 30 seconds; 72° C. for 30 seconds; x35 cycles; 72° C. for 3 minutes. BamHI enzyme was added to the PCR products and digestion carried out at 37° C. for 3 hours. The digested product was run on a 3% agarose gel which is sufficient to separate the digested products so that 200 bp and 182 bp bands can be distinguished.

Example 2

Elucidation of a Novel Splice Variant

Expression of an additional form of the S182 protein containing an insertion of four amino acids at codons 26–27

(VRSQ) was found. The VRSQ insertion arises from alternative use of a 5' exon donor site in the exon 3/intron 3 (−52 to 75 nt) boundary. (See FIG. 1). The . . . CAG/gta . . . boundary of the final Gln codon of exon 3 of the VRSQ motif provides the ideal 5' exon AG donor site and GT intron consensus 5' boundary and use of this splice site results in the insertion of the 12-nts encoding the VRSQ motif. The upstream . . . ACT/GTA . . . boundary of the Thr-Val codons provides the less preferred CT (AG preferred) 5' exonic boundary to the consensus GT 5' intronic boundary and splicing at this site would remove the VRSQ motif. Sherrington et al. *Nature* 1995, 375:754–760, reports the expression of only the VRSQ minus form. However, screening of fibroblasts with probes covering this region have shown that both splice variants are represented. Primers from the intronic region upstream (forward) and downstream exonic region of this alternate splicing sites allowed for their sequencing and elucidation.

Example 3

Elucidation of a Novel Splicing Between Exon 8 and 9

A mutation has been found in an early onset AD family designated F74 (it may also occur in another family, F184) in the last nucleotide of the intron between exons 8 and 9, G→T. This mutation spoils the acceptor site in the middle of Serine 857 and is expected to alter the splicing of this region. This mutation does not change the cDNA sequence and could, therefore, only be identified by sequencing of primers derived from intronic sequences.

Example 4:

Identification of E120K Mutation (G→A)

Additionally, a novel mutation was identified in exon 5 of S182 at codon 120 (lys→glu) arising from a G to A transition (GAA→AAA). This mutation is near the second putative transmembrane domain (TM2). This mutation is virtually impossible to detect without intronic sequence primers, as it is within 20 bp of the intron-exon boundary in genomic clones. E120K was found by PCR. A 100 μl reaction mix contained water, 10× buffer, 10 mM dNTP's, taq polymerase and 20 μM primer (5'-CCCAACCATAAGAAGAACAG-3' (SEQ ID NO: 19) and 5'-GTGGTAATGTGGTTGGTGAT-3' (SEQ ID NO: 20)). The PCR conditions were 94° C. for 5 minutes, (94° C. for 30 seconds, 50° C. for 30 seconds, 72° C. for 45 seconds) ×35, 72° C. for 10 minutes. The PCR products were electrophoresed on a 3% agarose gel and visualized by ethidium bromide. The biotinylated primer allows single stranded DNA to be derived using streptavidin-coated magnetic beads and sequenced on an ALF sequencer (Pharmacia) using Autoread kits (Pharmacia).

Example 5

Identification of L250S Mutation (T→C)

Family 184 was also screened for mutations by PCR. A 100 μl reaction mix contained water, 10X buffer, 5 mM dNTP's, taq polymerase and 20 μM primer (5'-AACAATGGTGTGGTTGGTGA-3' (SEQ ID NO: 21) and 5'-AAGTTTTGACATTAAGAGCT-3' (SEQ ID NO: 22)). The PCR conditions were 94° C. for 5 minutes, (94° C. for 30 seconds, 50° C. for 30 seconds, 72° C. for 45 seconds) ×35, 72° C. for 10 minutes. The PCR products were electrophoresed on a 3% agarose gel and visualized by ethidium bromide. The biotynilated primer allows single stranded DNA to be derived using streptavidin-coated magnetic beads and sequenced on an ALF sequencer (Pharmacia) using Autoread kits (Pharmacia). The base change T to C was found at codon 250 changing leucine to serine, by comparison with the normal PS 1 sequence.

```
                         SEQUENCE LISTING (1) GENERAL INFORMATION:

(iii) NUMBER OF SEQUENCES:  52

(2) INFORMATION FOR SEQ ID NO: 1:

(i) SEQUENCE CHARACTERISTICS:
         (A) LENGTH:  20
         (B) TYPE:  Nucleic Acid
         (C) STRANDEDNESS:  Single
         (D) TOPOLOGY:  Linear (iv) ANTI-SENSE:  No (xi) SEQUENCE DESCRIPTION:  SEQ ID NO: 1:

GTTTGTTTCT GCTTAATGTA                                                    20

(2) INFORMATION FOR SEQ ID NO: 2:

(i) SEQUENCE CHARACTERISTICS:
         (A) LENGTH:  21
         (B) TYPE:  Nucleic Acid
         (C) STRANDEDNESS:  Single
         (D) TOPOLOGY:  Linear
```

-continued

(iv) ANTI-SENSE: No

(xi) SEQUENCE DESCRIPTION: SEQ ID NO: 2:

GTTTTTTCTT TCCCTTTTCA G                     21

(2) INFORMATION FOR SEQ ID NO: 3:

(i) SEQUENCE CHARACTERISTICS:
    (A) LENGTH: 9
    (B) TYPE: Nucleic Acid
    (C) STRANDEDNESS: Single
    (D) TOPOLOGY: Linear   (iv) ANTI-SENSE: No   (xi) SEQUENCE DESCRIPTION: SEQ ID NO: 3:

GTACAGTGT                           9

(2) INFORMATION FOR SEQ ID NO: 4:

(i) SEQUENCE CHARACTERISTICS:
    (A) LENGTH: 20
    (B) TYPE: Nucleic Acid
    (C) STRANDEDNESS: Single
    (D) TOPOLOGY: Linear   (iv) ANTI-SENSE: No   (xi) SEQUENCE DESCRIPTION: SEQ ID NO: 4:

TGTTTTTCTT GTGCTTATAG                     20

(2) INFORMATION FOR SEQ ID NO: 5:

(i) SEQUENCE CHARACTERISTICS:
    (A) LENGTH: 18
    (B) TYPE: Nucleic Acid
    (C) STRANDEDNESS: Single
    (D) TOPOLOGY: Linear   (iv) ANTI-SENSE: No   (xi) SEQUENCE DESCRIPTION: SEQ ID NO: 5:

ACGTATGAGA TTTGTTTT                      18

(2) INFORMATION FOR SEQ ID NO: 6:

(i) SEQUENCE CHARACTERISTICS:
    (A) LENGTH: 20
    (B) TYPE: Nucleic Acid
    (C) STRANDEDNESS: Single
    (D) TOPOLOGY: Linear   (iv) ANTI-SENSE: No   (xi) SEQUENCE DESCRIPTION: SEQ ID NO: 6:

TTGTGTTTGT TTTATTGTAG                     20

(2) INFORMATION FOR SEQ ID NO: 7:

(i) SEQUENCE CHARACTERISTICS:
    (A) LENGTH: 20
    (B) TYPE: Nucleic Acid
    (C) STRANDEDNESS: Single
    (D) TOPOLOGY: Linear   (iv) ANTI-SENSE: No   (xi) SEQUENCE DESCRIPTION: SEQ ID NO: 7:

GTGAGCATGA GACACAGATC                                             20

(2) INFORMATION FOR SEQ ID NO: 8:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 8:

TGAAATGCTT TCTTTTCTAG                                             20

(2) INFORMATION FOR SEQ ID NO: 9:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 9:

GTAAAACCCA AGACTGATAA                                             20

(2) INFORMATION FOR SEQ ID NO: 10:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 10:

TTATGTTTTT CTTTTTCTAG                                             20

(2) INFORMATION FOR SEQ ID NO: 11:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 11:

GTATGTGCAT TTCTCTATGT                                             20

(2) INFORMATION FOR SEQ ID NO: 12:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 12:

TTGTAACCTT TCCTTTTTAG                                             20

(2) INFORMATION FOR SEQ ID NO: 13:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 13:

GTATGTGCAT TTCTCTATGT                                       20

(2) INFORMATION FOR SEQ ID NO: 14:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 14:

TTGTAACCTT TCCTTTTTAG                                       20

(2) INFORMATION FOR SEQ ID NO: 15:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 15:

GTAAGTATAC ACTAATAAGA                                       20

(2) INFORMATION FOR SEQ ID NO: 16:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 16:

CTTTCCCATC TTCTCCACAG                                       20

(2) INFORMATION FOR SEQ ID NO: 17:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 17:

CACCCATTTA CAAGTTTAGC                                       20

(2) INFORMATION FOR SEQ ID NO: 18:

(i) SEQUENCE CHARACTERISTICS:
        (A) LENGTH: 22
        (B) TYPE: Nucleic Acid

```
        (C) STRANDEDNESS:  Single
        (D) TOPOLOGY:  Linear (iv) ANTI-SENSE:  No (xi) SEQUENCE DESCRIPTION:  SEQ ID NO: 18:

CACTGATTAC TAATTCAGGA TC                                                22

(2) INFORMATION FOR SEQ ID NO: 19:

(i) SEQUENCE CHARACTERISTICS:
        (A) LENGTH:  20
        (B) TYPE:  Nucleic Acid
        (C) STRANDEDNESS:  Single
        (D) TOPOLOGY:  Linear (iv) ANTI-SENSE:  No (xi) SEQUENCE DESCRIPTION:  SEQ ID NO: 19:

CCCAACCATA AGAAGAACAG                                                   20

(2) INFORMATION FOR SEQ ID NO: 20:

(i) SEQUENCE CHARACTERISTICS:
        (A) LENGTH: 20
        (B) TYPE:  Nucleic Acid
        (C) STRANDEDNESS:  Single
        (D) TOPOLOGY:  Linear (iv) ANTI-SENSE:  No (xi) SEQUENCE DESCRIPTION:  SEQ ID NO: 20:

GTGGTAATGT GGTTGGTGAT                                                   20

(2) INFORMATION FOR SEQ ID NO: 21:

(i) SEQUENCE CHARACTERISTICS:
        (A) LENGTH:  20
        (B) TYPE:  Nucleic Acid
        (C) STRANDEDNESS:  Single
        (D) TOPOLOGY:  Linear (iv) ANTI-SENSE:  No (xi) SEQUENCE DESCRIPTION:  SEQ ID NO: 21:

AACAATGGTG TGGTTGGTGA                                                   20

(2) INFORMATION FOR SEQ ID NO: 22:

(i) SEQUENCE CHARACTERISTICS:
        (A) LENGTH:  20
        (B) TYPE:  Nucleic Acid
        (C) STRANDEDNESS:  Single
        (D) TOPOLOGY:  Linear (iv) ANTI-SENSE:  No (xi) SEQUENCE DESCRIPTION:  SEQ ID NO: 22:

AAGTTTTGAC ATTAAGAGCT                                                   20

(2) INFORMATION FOR SEQ ID NO: 23:

(i) SEQUENCE CHARACTERISTICS:
        (A) LENGTH:  30
        (B) TYPE:  Nucleic Acid
        (C) STRANDEDNESS:  Single
        (D) TOPOLOGY:  Linear (iv) ANTI-SENSE:  No
```

(xi) SEQUENCE DESCRIPTION: SEQ ID NO: 23:

ATAAAGAAAG GTTTGTTTCT GCTTAATGTA                              30

(2) INFORMATION FOR SEQ ID NO: 24:

(i) SEQUENCE CHARACTERISTICS:
        (A) LENGTH: 31
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 24:

GTTTTTTCTT TCCCTTTTCA GAACCTCAAG A                             31

(2) INFORMATION FOR SEQ ID NO: 25:

(i) SEQUENCE CHARACTERISTICS:
        (A) LENGTH: 30
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 25:

AGCAATACTG TACGTAGCCA GGTACAGTGT                              30

(2) INFORMATION FOR SEQ ID NO: 26:

(i) SEQUENCE CHARACTERISTICS:
        (A) LENGTH: 29
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 26:

TGTTTTTCTT GTGCTTATAG AATGACAAT                               29

(2) INFORMATION FOR SEQ ID NO: 27:

(i) SEQUENCE CHARACTERISTICS:
        (A) LENGTH: 28
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 27:

GGGCAGCTGT ACGTATGAGA TTTGTTTT                                28

(2) INFORMATION FOR SEQ ID NO: 28:

(i) SEQUENCE CHARACTERISTICS:
        (A) LENGTH: 29
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 28:

TTGTGTTTGT TTTATTGTAG AATCTATAC                               29

(2) INFORMATION FOR SEQ ID NO: 29:

(i) SEQUENCE CHARACTERISTICS:
        (A) LENGTH: 29
        (B) TYPE: Nucleic Acid
        (C) STRANDEDNESS: Single
        (D) TOPOLOGY: Linear     (iv) ANTI-SENSE: No     (xi) SEQUENCE DESCRIPTION: SEQ ID NO: 29:

TGCTATAAGG TGAGCATGAG ACACAGATC                                                           29

(2) INFORMATION FOR SEQ ID NO: 30:

(i) SEQUENCE CHARACTERISTICS:
        (A) LENGTH: 29
        (B) TYPE: Nucleic Acid
        (C) STRANDEDNESS: Single
        (D) TOPOLOGY: Linear     (iv) ANTI-SENSE: No     (xi) SEQUENCE DESCRIPTION: SEQ ID NO: 30:

TGAAATGCTT TCTTTTCTAG GTCATCCAT                                                           29

(2) INFORMATION FOR SEQ ID NO: 31:

(i) SEQUENCE CHARACTERISTICS:
        (A) LENGTH: 28
        (B) TYPE: Nucleic Acid
        (C) STRANDEDNESS: Single
        (D) TOPOLOGY: Linear     (iv) ANTI-SENSE: No     (xi) SEQUENCE DESCRIPTION: SEQ ID NO: 31:

TACTTGGGGT AAGTTGTGAA ATTTTTGG                                                             28

(2) INFORMATION FOR SEQ ID NO: 32:

(i) SEQUENCE CHARACTERISTICS:
        (A) LENGTH: 29
        (B) TYPE: Nucleic Acid
        (C) STRANDEDNESS: Single
        (D) TOPOLOGY: Linear     (iv) ANTI-SENSE: No     (xi) SEQUENCE DESCRIPTION: SEQ ID NO: 32:

TCTGTGTAAT TTTTTTTCAG GGAACTGTT                                                       29

(2) INFORMATION FOR SEQ ID NO: 33:

(i) SEQUENCE CHARACTERISTICS:
        (A) LENGTH: 30
        (B) TYPE: Nucleic Acid
        (C) STRANDEDNESS: Single
        (D) TOPOLOGY: Linear     (iv) ANTI-SENSE: No     (xi) SEQUENCE DESCRIPTION: SEQ ID NO: 33:

TCAGTATATG GTAAAACCCA AGACTGATAA                                            30

(2) INFORMATION FOR SEQ ID NO: 34:

(i) SEQUENCE CHARACTERISTICS:
              (A) LENGTH:  29
              (B) TYPE:  Nucleic Acid
              (C) STRANDEDNESS:  Single
              (D) TOPOLOGY:  Linear (iv) ANTI-SENSE:  No (xi) SEQUENCE DESCRIPTION:  SEQ ID NO: 34:

TTATGTTTTT CTTTTTCTAG ATTTAGTGG                                              29

(2) INFORMATION FOR SEQ ID NO: 35:

(i) SEQUENCE CHARACTERISTICS:
              (A) LENGTH:  30
              (B) TYPE:  Nucleic Acid
              (C) STRANDEDNESS:  Single
              (D) TOPOLOGY:  Linear (iv) ANTI-SENSE:  No (xi) SEQUENCE DESCRIPTION:  SEQ ID NO: 35:

ATTTACTCCT GTAAGTATTT GAGAAGGATA                                             30

(2) INFORMATION FOR SEQ ID NO: 36:

(i) SEQUENCE CHARACTERISTICS:
              (A) LENGTH:  28
              (B) TYPE:  Nucleic Acid
              (C) STRANDEDNESS:  Single
              (D) TOPOLOGY:  Linear (iv) ANTI-SENSE:  No (xi) SEQUENCE DESCRIPTION:  SEQ ID NO: 36:

AATTTNGTCT TTCCCAACAG CAACAATG                                               28

(2) INFORMATION FOR SEQ ID NO: 37:

(i) SEQUENCE CHARACTERISTICS:
              (A) LENGTH:  30
              (B) TYPE:  Nucleic Acid
              (C) STRANDEDNESS:  Single
              (D) TOPOLOGY:  Linear (iv) ANTI-SENSE:  No (xi) SEQUENCE DESCRIPTION:  SEQ ID NO: 37:

AATGCAGAAA GTAGGTAACT TTTATTAGAT                                             30

(2) INFORMATION FOR SEQ ID NO: 38:

(i) SEQUENCE CHARACTERISTICS:
              (A) LENGTH:  28
              (B) TYPE:  Nucleic Acid
              (C) STRANDEDNESS:  Single
              (D) TOPOLOGY:  Linear (iv) ANTI-SENSE:  No (xi) SEQUENCE DESCRIPTION:  SEQ ID NO: 38:

ACTTCCACTT TCTCTTGAAG CACAGAAG                                               28

(2) INFORMATION FOR SEQ ID NO: 39:

(i) SEQUENCE CHARACTERISTICS:
              (A) LENGTH:  30
              (B) TYPE:  Nucleic Acid
              (C) STRANDEDNESS:  Single (D) TOPOLOGY:  Linear (iv) ANTI-SENSE:  No (xi) SEQUENCE DESCRIPTION: SEQ ID NO: 39:

CCAGAGGAAA GTATGTGCAT TTCTCTATGT                                              30

(2) INFORMATION FOR SEQ ID NO: 40:

(i) SEQUENCE CHARACTERISTICS:
        (A) LENGTH:  28
        (B) TYPE:  Nucleic Acid
        (C) STRANDEDNESS:  Single
        (D) TOPOLOGY:  Linear (iv) ANTI-SENSE:  No (xi) SEQUENCE DESCRIPTION: SEQ ID NO: 40:

TTGTAACCTT TCCTTTTTAG GGGGAGTA                                                28

(2) INFORMATION FOR SEQ ID NO: 41:

(i) SEQUENCE CHARACTERISTICS:
        (A) LENGTH:  29
        (B) TYPE:  Nucleic Acid
        (C) STRANDEDNESS:  Single
        (D) TOPOLOGY:  Linear (iv) ANTI-SENSE:  No (xi) SEQUENCE DESCRIPTION: SEQ ID NO: 41:

ATATTAATTG TAAGTATACA CTAATAAGA                                               29

(2) INFORMATION FOR SEQ ID NO: 42:

(i) SEQUENCE CHARACTERISTICS:
        (A) LENGTH:  29
        (B) TYPE:  Nucleic Acid
        (C) STRANDEDNESS:  Single
        (D) TOPOLOGY:  Linear (iv) ANTI-SENSE:  No (xi) SEQUENCE DESCRIPTION: SEQ ID NO: 42:

CTTTCCCATC TTCTCCACAG GGTTTGTGC                                               29

(2) INFORMATION FOR SEQ ID NO: 43:

(i) SEQUENCE CHARACTERISTICS:
        (A) LENGTH:  18
        (B) TYPE:  Nucleic Acid
        (C) STRANDEDNESS:  Single
        (D) TOPOLOGY:  Linear (iv) ANTI-SENSE:  No (xi) SEQUENCE DESCRIPTION: SEQ ID NO: 43:

ATTTACTCCT CAACAATG                                                           18

(2) INFORMATION FOR SEQ ID NO: 44:

(i) SEQUENCE CHARACTERISTICS:
        (A) LENGTH:  18
        (B) TYPE:  Nucleic Acid
        (C) STRANDEDNESS:  Single
        (D) TOPOLOGY:  Linear (iv) ANTI-SENSE:  No

```
    (xi) SEQUENCE DESCRIPTION: SEQ ID NO: 44:

AATGCAGAAA GCACAGAA                                                18

(2) INFORMATION FOR SEQ ID NO: 45:

(i) SEQUENCE CHARACTERISTICS:
        (A) LENGTH: 18
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 45:

ATTTACTCCT GCACAGAA                                                18

(2) INFORMATION FOR SEQ ID NO: 46:

(i) SEQUENCE CHARACTERISTICS:
        (A) LENGTH: 18
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 46:

CCAGAGGAAA GGGGAGTA                                                18

(2) INFORMATION FOR SEQ ID NO: 47:

(i) SEQUENCE CHARACTERISTICS:
        (A) LENGTH: 12
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 47:

CAACAGCAAC AA                                                      12

(2) INFORMATION FOR SEQ ID NO: 48:

(i) SEQUENCE CHARACTERISTICS:
        (A) LENGTH: 12
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 48:

CAACATCAAC AA                                                      12

(2) INFORMATION FOR SEQ ID NO: 49:

(i) SEQUENCE CHARACTERISTICS:
        (A) LENGTH: 6
        (B) TYPE: Amino Acid
        (D) TOPOLOGY: Linear (xi) SEQUENCE DESCRIPTION: SEQ ID NO: 49:

ILE TYR SER SER THR MET
1               5

(2) INFORMATION FOR SEQ ID NO: 50:
```

-continued

```
    (i) SEQUENCE CHARACTERISTICS:
        (A) LENGTH: 6
        (B) TYPE:  Amino Acid
        (D) TOPOLOGY:  Linear (xi) SEQUENCE DESCRIPTION:  SEQ ID NO: 50:

ASN ALA GLU SER THR GLU
1               5

(2) INFORMATION FOR SEQ ID NO: 51:

(i) SEQUENCE CHARACTERISTICS:
        (A) LENGTH: 6
        (B) TYPE:  Amino Acid
        (D) TOPOLOGY:  Linear (xi) SEQUENCE DESCRIPTION:  SEQ ID NO: 51:

ILE TYR SER CYS THR GLU
1               5

(2) INFORMATION FOR SEQ ID NO: 52:

(i) SEQUENCE CHARACTERISTICS:
        (A) LENGTH: 6
        (B) TYPE:  Amino Acid
        (D) TOPOLOGY:  Linear (xi) SEQUENCE DESCRIPTION:  SEQ ID NO: 52:

PRO GLU GLU ARG GLY VAL
1               5
```

What is claimed:

1. A method of detecting intronic polymorphisms S182 gene comprising:
   (a) amplifying portions of the S182 gene using selected primers in polymerase chain reaction amplification, said primers comprising intronic sequences of the S182 gene to provide an amplified product; and
   (b) comparing the amplified product from said amplification to the wild type S182 gene to detect said intronic polymorphisms.

2. The method of claim 1 wherein the primers comprise SEQ ID NOS: 21 and 22.

3. The method of claim 1 wherein the primers comprise SEQ ID NOS: 19 and 20.

4. The method of claim 1 wherein the primers comprise SEQ ID NOS: 17 and 18.

5. A method of identifying an individual with an increased likelihood of developing late onset Alzheimer's Disease comprising:
   (a) providing a sample of genetic material from an individual susceptible to late onset Alzheimer's Disease;
   (b) detecting the L2505 mutation in the S182 gene in the sample of genetic material using selected primers in polymerase chain reaction amplification, wherein said primers comprise SEQ ID NOS: 21 and 22 to provide an amplified product;
   (c) comparing the amplified product of said amplification to the wild type S182 gene to detect said mutation; and
   (d) correlating the detected, mutation to identification of individuals with an increased likelihood of developing late onset Alzheimer's Disease.

6. A method of identifying an individual with an increased likelihood of developing late onset Alzheimer's Disease comprising:
   (a) providing a sample of genetic material from an individual susceptible to late onset Alzheimei's Disease;
   (b) detecting the E120K mutation in the S182 gene in the sample of genetic material using selected primers in polymerase chain reaction amplification, wherein said primers comprise SEQ ID NOS: 19 and 20 to provide an amplified product;
   (c) comparing the amplified product of said amplification to the wild type S182 gene to detect said mutation; and
   (d) correlating the detected mutation to identification of individuals with an increased likelihood of developing late onset Alzheimer's Disease.

7. A method of identifying an individual with an increased likelihood of developing late onset Alzheimer's Disease comprising:
   (a) providing a sample of genetic material from an individual susceptible to late onset Alzheimer's Disease;
   (b) detecting variants in the S182 gene in the sample of genetic material using selected primers in polymerase chain reaction amplification, wherein said primers comprise SEQ ID NOS: 17 and 18 to provide an amplified product;
   (c) determining the size of the amplified product of step (c) to detect said variants; and
   (d) correlating the detected variants to identification of individuals with an increased likelihood of developing late onset Alzheimer's Disease.

* * * * *